United States Patent
Sara (10) Patent No.: US 10,799,280 B2
(45) Date of Patent: Oct. 13, 2020

(54) POST ABLATION TISSUE ANALYSIS TECHNIQUE

(71) Applicant: Medtronic CryoCath LP, Toronto (CA)

(72) Inventor: Rahmani Sara, Montreal (CA)

(73) Assignee: Medtronic CryoCath LP, Toronto, Ontario ( * ) Notice: Subject to any disclaimer, the term of this patent is extended or adjusted under 35 U.S.C. 154(b) by 1104 days.

(21) Appl. No.: 14/920,356

(22) Filed: Oct. 22, 2015

(65) Prior Publication Data

US 2017/0112558 A1   Apr. 27, 2017

(51) Int. Cl.
*A61B 18/02* (2006.01)
*A61B 5/00* (2006.01)
(Continued)

(52) U.S. Cl.
CPC .......... *A61B 18/02* (2013.01); *A61B 5/0036* (2018.08); *A61B 5/0075* (2013.01);
(Continued)

(58) Field of Classification Search
CPC .. A61B 2018/0022; A61B 2018/00636; A61B 2018/00934; A61B 2090/3735
See application file for complete search history.

(56) References Cited

U.S. PATENT DOCUMENTS

| | | | |
|---|---|---|---|
| 8,235,976 B2 * | 8/2012 | Lafontaine | A61B 18/02 606/20 |
| 9,014,789 B2 | 4/2015 | Mercader et al. | |

(Continued)

FOREIGN PATENT DOCUMENTS

| | | |
|---|---|---|
| CN | 104066368 A | 9/2014 |
| CN | 108135645 A | 6/2018 |

(Continued)

OTHER PUBLICATIONS

Alejandro Martinez-Rios, David Monzon-Hernandez, Ismael Torres-Gomez and Guillermo Salceda-Delgado (2012). Long Period Fibre Gratings, Fiber Optic Sensors, Dr Moh. Yasin (Ed.), ISBN: 978-953-307-922-6, InTech http://www.intechopen.com/books/fiber-optic-sensors/long-period-fibre-gratings (Year: 2012).*

(Continued)

*Primary Examiner* — Michael F Peffley
*Assistant Examiner* — Bo Ouyang
(74) *Attorney, Agent, or Firm* — Christopher & Weisberg, P.A.

(57) ABSTRACT

A device, system, and method for identifying an area of ablated tissue. Specifically, the device, system, and method may include a device having one or more fiber sensors and a processing unit for receiving emitted and/or reflected light from tissue and making one or more determinations based on the received light regarding ablated tissue, tissue contact, and/or occlusion. Each of the fiber sensors may include at least one multimode waveguide segment and at least one singlemode waveguide segment, or each of the fiber sensors may be singlemode waveguide. Further, each fiber sensor may have a core with long-period grating for optically coupling light from tissue to the fiber sensor. The processing unit may include a beam processing apparatus and a hyperspectral imaging and analysis apparatus, and may optionally include a light source.

17 Claims, 10 Drawing Sheets

(51) Int. Cl.
  *A61B 5/053* (2006.01)
  *A61B 18/14* (2006.01)
  *A61B 17/00* (2006.01)
  *A61B 18/00* (2006.01)

(52) U.S. Cl.
  CPC .......... *A61B 5/0535* (2013.01); *A61B 5/0538* (2013.01); *A61B 5/4836* (2013.01); *A61B 18/1492* (2013.01); *A61B 5/0084* (2013.01); *A61B 2017/00061* (2013.01); *A61B 2018/0022* (2013.01); *A61B 2018/00351* (2013.01); *A61B 2018/00577* (2013.01); *A61B 2018/00642* (2013.01); *A61B 2018/00755* (2013.01); *A61B 2018/00839* (2013.01); *A61B 2018/00875* (2013.01); *A61B 2018/0212* (2013.01)

(56) References Cited

U.S. PATENT DOCUMENTS

| | | |
|---|---|---|
| 2006/0122587 A1 | 6/2006 | Sharareh |
| 2006/0135870 A1* | 6/2006 | Webler ................. A61B 5/0062 600/431 |
| 2006/0229515 A1 | 10/2006 | Sharareh et al. |
| 2007/0078450 A1 | 4/2007 | Langer |
| 2007/0232871 A1 | 10/2007 | Sinofsky et al. |
| 2008/0021275 A1* | 1/2008 | Tearney ............... A61B 5/0062 600/115 |
| 2009/0005771 A1* | 1/2009 | Lieber ................ A61B 18/1492 606/34 |
| 2009/0143774 A1 | 6/2009 | Uzunbajakava et al. |
| 2010/0228238 A1* | 9/2010 | Brennan .............. A61B 5/0066 606/13 |
| 2012/0271339 A1* | 10/2012 | O'Beirne ........... A61M 25/104 606/194 |
| 2014/0276709 A1* | 9/2014 | Wittenberger ..... A61B 18/1492 606/23 |
| 2015/0141847 A1* | 5/2015 | Sarvazyan ........... A61B 5/0075 600/478 |

FOREIGN PATENT DOCUMENTS

| | | |
|---|---|---|
| WO | 199838907 A1 | 9/1998 |
| WO | 2013123020 A1 | 8/2013 |
| WO | 2015056662 A1 | 4/2015 |
| WO | 2015128179 A1 | 9/2015 |
| WO | 2015128218 A1 | 9/2015 |

OTHER PUBLICATIONS

International Search Report and Written Opinion dated Jan. 17, 2017, for corresponding International Application No. PCT/CA2016/051206; International Filing Date: Oct. 18, 2016 consisting of 8 pages.

China National Intellectual Property Adminstration, Chinese Office Action, dated Apr. 16, 2020 for corresponding Chinese Application No. 201680061805.4, 32 pages.

* cited by examiner

POST ABLATION TISSUE ANALYSIS TECHNIQUE

CROSS-REFERENCE TO RELATED APPLICATION n/a

STATEMENT REGARDING FEDERALLY SPONSORED RESEARCH OR DEVELOPMENT n/a

TECHNICAL FIELD

The present invention relates to a device, system, and method for identifying an area of ablated tissue. The present invention also relates to a device, system, and method for assessing contact between a treatment element and tissue and/or assessing occlusion of a body lumen by the treatment element. Specifically, the device, system, and method may include one or more fiber sensors and a processing unit for receiving emitted and/or reflected light from tissue and making one or more determinations based on the received light regarding ablated tissue, tissue contact, and/or occlusion.

BACKGROUND

A cardiac arrhythmia is a condition in which the heart's normal rhythm is disrupted. Certain types of cardiac arrhythmias, including ventricular tachycardia and atrial fibrillation, may be treated by ablation (for example, radiofrequency (RF) ablation, cryoablation, ultrasound ablation, laser ablation, microwave ablation, and the like), either endocardially or epicardially.

Procedures such as pulmonary vein isolation (PVI) and pulmonary vein antrum isolation (PVAI) are commonly used to treat atrial fibrillation. These procedures generally involve the use of a cryogenic device, such as a catheter, which is positioned at the ostium of a pulmonary vein (PV) such that any blood flow exiting the PV into the left atrium (LA) is completely blocked. Once in position, the cryogenic device may be activated for a sufficient duration to create a desired lesion within myocardial tissue at the PV-LA junction, such as a PV ostium or PV antrum. If a cryoballoon is used as the treatment element of the cryogenic device, the balloon is typically inflated using a fluid refrigerant, enabling an entire outer diameter of the balloon to create a circumferential lesion about the ostium and/or antrum of the PV to disrupt aberrant electrical signals exiting the PV. Additionally or alternatively, the cryoballoon may also be used to treat cardiac wall tissue (for example, left atrial wall tissue), in which case the cryoballoon is positioned in contact with the target tissue.

The success of this procedure depends largely on the quality of the lesion(s) created during the procedure, as incomplete isolation may result in late recurrence of AF. At present, the main indicator of ablation completeness is the measure of the electrical isolation of focal sources. It is known that this method is limited by the fact that the extent of the lesions cannot be measured during the ablation and that the specific cause of the electrical isolation cannot be determined. Therefore, it is crucial to assess the completeness of the isolation, which eliminates the need for redundant surgeries and reduces procedure time. It therefore would be beneficial to monitor the spectrum of the tissue being treated, in part as an indication of lesion quality.

Some systems require transmitting light from a device to the tissue and collecting the reflected and diffracted light by the device and/or one or more system components. It is known that the light absorption induces a heat effect at the cellular level, and temperature is directly related to the excitation of molecules, and thus emission of spectral signals is different than in unexcited cells. If the temperature is raised above a defined level, DNA, RNA, and some proteins may denature and coagulate as a result. Further, when light is transmitted to the tissue, a portion of the light is reflected, another portion is scattered, another portion is absorbed, and yet another portion is transmitted further. The scattering is the result of light rays being redirected due to refractive index variability within tissue, and limits the depth of light penetration within the tissue. Scattering is inversely proportional to the square of the wavelength of light.

Infrared imaging may be used in medical procedures to detect cancerous or abnormal cells, which have different temperature signatures, by measuring the emitted infrared radiation from the cells. Ambient objects radiate energy in the infrared spectral region with wavelengths ranging from 2 to 12 microns, depending on the objects inherent temperature. Abnormal cells radiate slightly differently than normal cells, allowing the abnormal cells to be imaged as objects of distinct color. This principal is commonly used in mammography. When breast tissue is photographed with an infrared camera, cancerous tissue is distinguished as having a different gray level (color), indicating tissue of a different temperature at that location. However, the use of infrared imaging within the body using endoscopes, for example, has limitations.

Endoscopes are also sometimes used to measure cancer characteristics in internal body cavities. However, infrared endoscopes face limitations when used to image internal body cavities containing liquids (for example, blood, body water, vitreous humor, etc.). Water is not transparent to infrared radiation for most wavelengths.

Therefore, it is desirable to provide a cryoablation system and device that allows for the real-time lesion formation assessment by providing real-time spectral feedback during a cryotreatment procedure.

SUMMARY

The present invention advantageously provides a method and system for identifying an area of ablated tissue. A device may generally include: an elongate body including a distal portion and a proximal portion: an inflatable treatment element, at least a portion of the inflatable treatment element being coupled to the distal portion of the elongate body; and a fiber sensor having a distal portion and a proximal portion, at least a portion of the fiber sensor being located within the inflatable treatment element, the fiber sensor being slidably disposed within the shaft. The inflatable treatment element may define an interior surface, and the fiber sensor may be configured to be in contact with at least a portion of the interior surface when the inflatable treatment element is inflated. The device may further include a shaft having a proximal portion and a distal portion, the shaft being longitudinally movable within the elongate body and at least a portion of the distal portion of the shaft being located within the inflatable treatment element. The shaft may include a distal portion and the inflatable treatment element may include a proximal neck and a distal neck, the distal neck being coupled to the distal portion of the shaft and the proximal neck being coupled to the distal portion of the elongate body. The device may further include a handle coupled to the proximal portion of the elongate body, the handle including a rotary mechanism, the proximal portion of the fiber sensor being engaged with the rotary mechanism. The fiber sensor may include at least one singlemode waveguide segment and at least one multimode waveguide segment. For example, the fiber sensor may include a first singlemode waveguide segment, a second singlemode waveguide segment, a third singlemode waveguide segment, a first multimode waveguide segment, and a second multimode waveguide segment. In this case, the first multimode waveguide segment may be located between the first singlemode waveguide segment and the second singlemode waveguide segment, and the second multimode waveguide segment may be located between the second singlemode waveguide segment and the third singlemode waveguide segment. The inflatable treatment element may further include an outer surface that is configured to be in contact with an area of target tissue when the inflatable element is inflated.

A medical device for determining whether an area of tissue has been ablated may generally include: an elongate body having a distal portion, a proximal portion, and a longitudinal axis; an inflatable treatment element at the distal portion of the elongate body; a shaft defining a lumen and having a distal portion and a proximal portion, at least a portion of the shaft being located within the inflatable treatment element; and a first fiber sensor and a second fiber sensor each configured to transmit optical data from the area of tissue, at least a portion of each of the first and the second fiber sensors being located within the inflatable treatment element and having a core and a cladding, the core of each of the first and the second fiber sensors having an optical grating. Each of the first and the second fiber sensors may be a multimode waveguide. Further, each of the first and the second fiber sensors may be longitudinally movable within the shaft. The inflatable treatment element may define an inner surface and an outer surface, and the cladding of each of the first and the second fiber sensors may be configured to be in contact with the inner surface when the inflatable treatment element is inflated. Light from the tissue may be coupled from the inflatable treatment element to the cladding of at least one of the first and the second fiber sensors at an area of contact between the at least one of the first and the second fiber sensors and the inflatable treatment element. The optical grating may include a period Λ (nm), the period Λ being selected according to the equation:

$$\Lambda \text{ (nm)} = \lambda/(n_{\it eff}\text{Core} - n_{\it eff}\text{CL}),$$

wherein $n_{\it eff}$Core is an effective refractive index of the core, $n_{\it eff}$CL is an effective refractive index of the cladding 86, and λ is the resonant wavelength of the light from the tissue.

A medical system for determining whether an area of tissue has been ablated may include: a device including: an elongate body having a distal portion, a proximal portion, and a longitudinal axis; an inflatable treatment element at the distal portion of the elongate body; a shaft defining a lumen and having a distal portion and a proximal portion, at least a portion of the shaft being located within the inflatable treatment element; and at least one fiber sensor configured to transmit optical data from the area of tissue, at least a portion of the at least one fiber sensor being located within the inflatable treatment element and having a core and a cladding, the core of each of the first and second fiber sensors having a long-period grating. The system may also include a processing unit in communication with the at least one fiber sensor, the processing unit including: a beam processing apparatus configured to receive optical data transmitted through the fiber sensor; and a hyperspectral imaging and analysis apparatus in communication with the beam processing apparatus and configured to generate a hyperspectral image based on the optical data received by the beam processing apparatus. The beam processing apparatus may include a grating and a broadband infrared detector. The beam processing apparatus may be configured to convert an optical signal received from the fiber sensor to an electrical signal including a plurality of pixels, and further may be configured to correlate each pixel to a spectrum value. The hyperspectral imaging and analysis apparatus may be configured to compare the spectrum value of each pixel to a reference spectrum value of ablated tissue, and may be configured to determine whether the area tissue is ablated based at least in part on the comparison.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

The present invention relates to a device, system, and method for identifying an area of ablated tissue. The present invention also relates to a device, system, and method for assessing contact between a treatment element and tissue and/or assessing occlusion of a body lumen by the treatment element. Specifically, the device, system, and method may include one or more fiber sensors and a processing unit for receiving emitted and/or reflected light from tissue and making one or more determinations based on the spectral differences between the ablated and non-ablated tissue.

Figure 1:
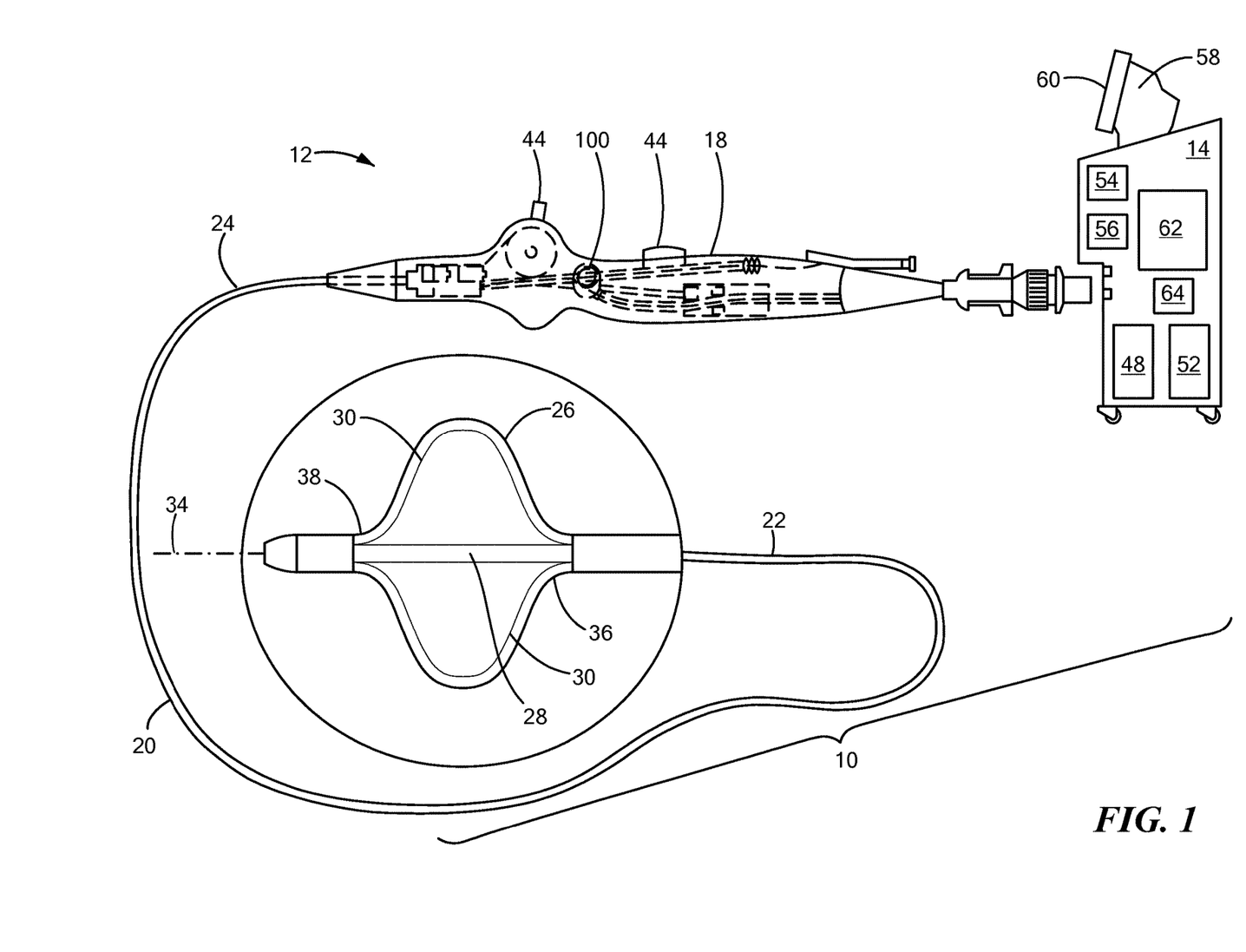
FIG. 1 shows an exemplary cryotreatment system that includes a device having at least one fiber sensor.
Figure 2:
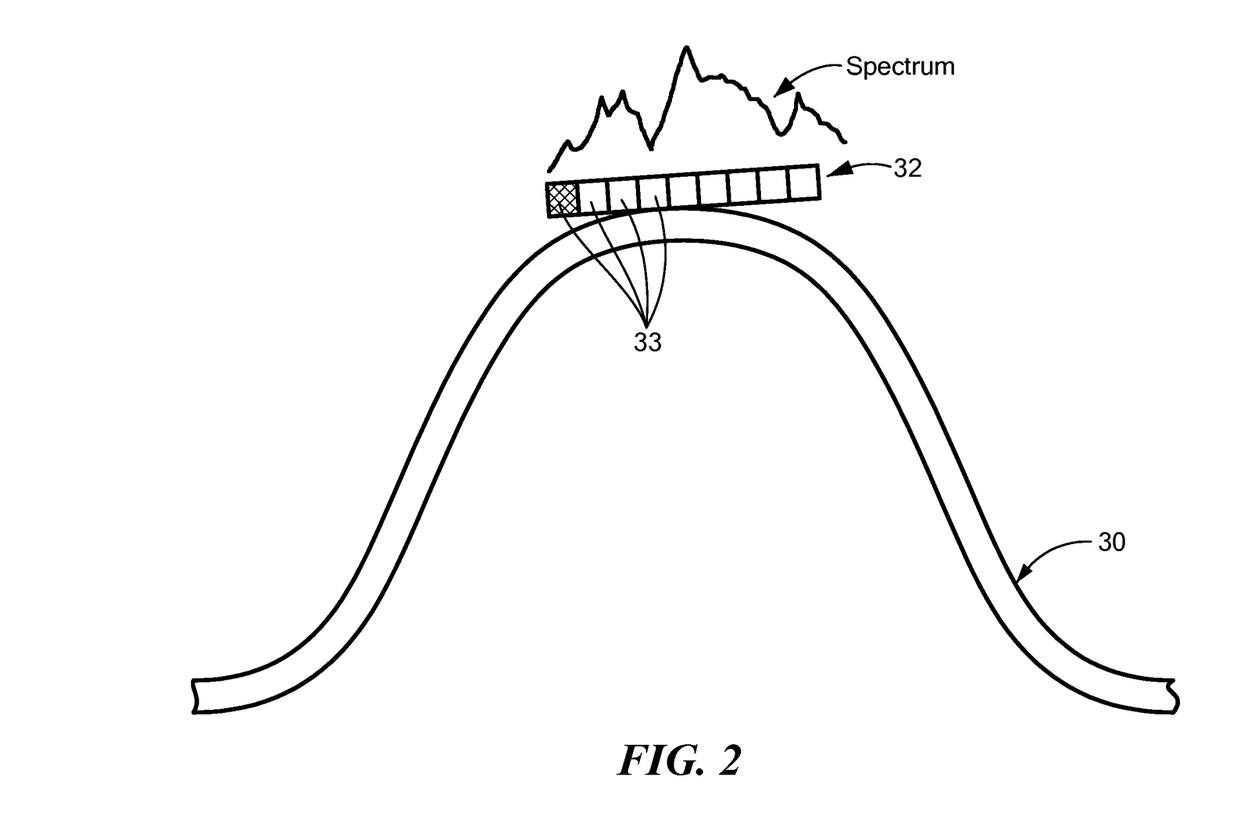
FIG. 2 shows a schematic view of a fiber sensor and the correlation of each pixel of a hypercube swath to a portion of the electromagnetic spectrum.

Referring now to FIG. 1, an exemplary cryotreatment system that includes a device having a fiber sensor for hyperspectral data acquisition is shown. Hyperspectral data acquisition may include scanning the tissue surface and collecting images along the electromagnetic spectrum. This may constitute a dataset referred to as a hypercube that includes layered images along the electromagnetic spectrum from ultraviolet to long infrared wavelength, with each layer of the hypercube corresponding to a wavelength band. The fiber sensor 30 covers an arrow of the hypercube (that is, a spatial line or swath 32) and each pixel 33 of this arrow consists of a wavelength band of the electromagnetic spectrum (for example, as shown in FIG. 2). A revolve scan with the fiber sensor over a wide angle may create a push-broom image that provides diagnostic information about the composition of the tissue. If the sensor spatial resolution is not high enough, disparate features might jointly occupy a single pixel 33. Therefore, the acquired wavelengths might be the composite of individual wavelengths, referred to as a mixed pixel. Mixed pixels may occur, for example, when thermal gaps exist within the ablated tissue between the ablated and non-ablated sections are combined into a homogenous mixture. In this case, a spectral "unmixing" algorithm may be used to decompose the mixed pixels into a collection of distinct wavelengths. Thus, one aspect of the spectral unmixing of a hyperspectral dataset may be discernment between ablated and non-ablated spots within the tissue. Alternatively, the collected wavelengths may be compared to a library of spectral data collected using in-vitro assessment of the targeted tissue.

The system 10 may generally include a treatment device, such as a cryotreatment catheter 12, for thermally treating an area of tissue, and a console 14 that houses various system 10 controls. The system 10 may be adapted for a cryotreatment procedure, such as cryoablation. The system 10 may additionally be adapted for radiofrequency (RF) ablation and/or phased RF ablation, ultrasound ablation, laser ablation, microwave ablation, hot balloon ablation, or other ablation methods or combinations thereof.

Figure 7:
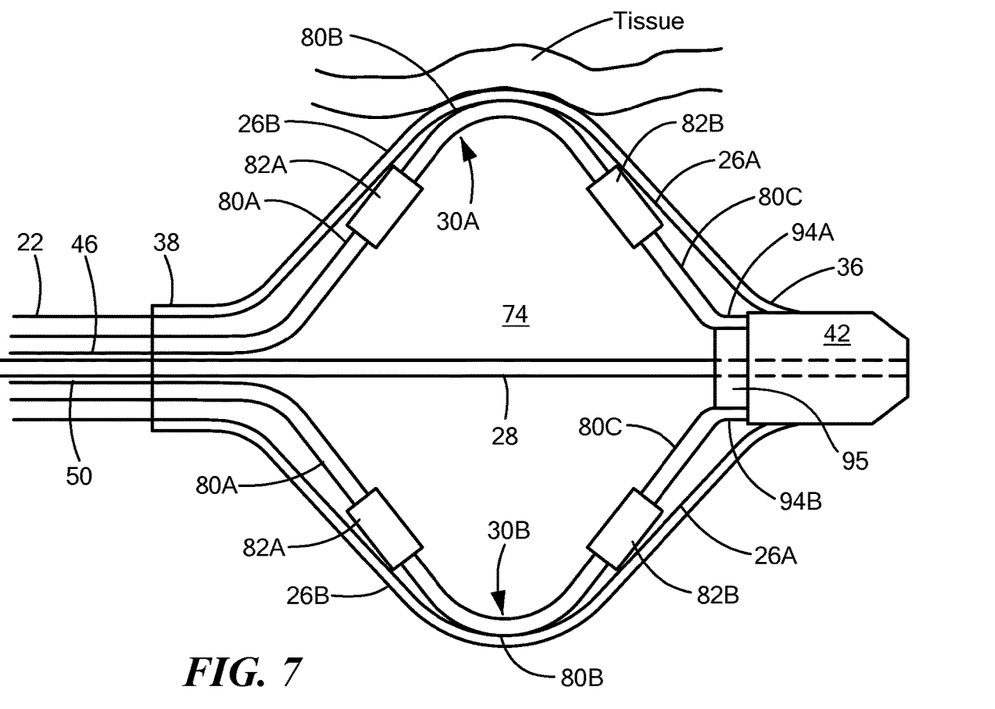
FIG. 7 shows a cross-sectional view of a cryotreatment device having a first fiber sensor and a second fiber sensor according to a first embodiment, the cryotreatment device positioned in direct contact with an area of tissue.

The cryotreatment catheter 12 may generally include a handle 18, an elongate body 20 having a distal portion 22 and a proximal portion 24, one or more inflatable treatment elements such as a cryoballoon 26, a shaft 28 (for example, a guidewire lumen), and one or more fiber sensors 30, which may be referred to herein as "waveguides." Further, the cryotreatment catheter 12 may have a longitudinal axis 34. The treatment element may be a cryoballoon 26 coupled to the distal portion 22 of the elongate body 20 of the cryotreatment catheter 12. For example, the cryoballoon 26 may define a proximal portion or neck 36 that is affixed to or coupled to the distal portion 22 of the elongate body 20, and may further define a distal portion or neck 38 that is affixed to or coupled to the shaft 28 (such as the distal portion 40 of the shaft 28). However, it will be understood that the cryoballoon 26 may be coupled, affixed, disposed on, integrated with, or otherwise attached to the elongate body 20 and/or the shaft 28. Additionally, multiple cryoballoons may be used, such as when the cryoballoon 26A is disposed within a second cryoballoon 26B (as shown in FIG. 7). The shaft 28 may lie along the longitudinal axis 34 and longitudinally movable or slidable within the elongate body 20. In this manner, longitudinal movement of the shaft 28 will affect the shape of the cryoballoon 26. The proximal portion of the shaft 28 may be in mechanical communication with one or more steering mechanisms 44 in the handle 18 of the cryotreatment catheter 12, such that the shaft 28 may be longitudinally extended or retracted using one or more steering mechanisms 44, such as knobs, levers, wheels, pull cords, and the like.

In addition to the shaft 28, the cryotreatment catheter 12 may include one or more lumens. As shown in FIG. 7, the cryotreatment catheter 12 may include a refrigerant injection lumen 46 in fluid communication with a refrigerant supply reservoir 48, and a refrigerant recovery lumen 50 in fluid communication with a refrigerant recovery reservoir 52. Further, the refrigerant recovery lumen 50 may be in communication with a vacuum 54 to facilitate removal of fluid from the cryoballoon 26 (for example, expanded refrigerant). If the cryotreatment catheter 12 includes thermoelectric cooling elements or electrodes capable of transmitting radiofrequency (RF), ultrasound, microwave, electroporation energy, or the like, the elongate body 18 may include a lumen in electrical communication with an energy generator 56.

The console 14 may be in electrical and fluid communication with the cryotreatment catheter 12 and may include one or more fluid (for example, cryotreatment refrigerant) reservoirs 48, refrigerant recovery reservoirs 52, energy generators 56, and computers 58 with displays 60, and may further include various other screens, user input controls, keyboards, buttons, valves, conduits, connectors, power sources, processors, and computers for adjusting and monitoring system 10 parameters. As used herein, the term "computer" may refer to any programmable data-processing unit, including a smart phone, dedicated internal circuitry, user control device, or the like. The computer 58 may be in electrical and/or wireless communication with a processing unit 62 that is in optical communication with the one or more fiber sensors 30. The computer 58 may further be in communication with the one or more treatment elements 26 and one or more system valves (not shown). The processing unit 62 and/or the computer may be programmable to execute an algorithm for hyperspectral data acquisition and analysis and for generating one or more displays or alerts to notify the user of various system criteria or determinations. As a non-limiting embodiment, the proximal portion of the cryotreatment catheter 12 may include an electrical connection that is matable to at least a portion of the console (for example, with the electrophysiology recording equipment) and in electrical communication with the processing unit 62.

Figure 3A:
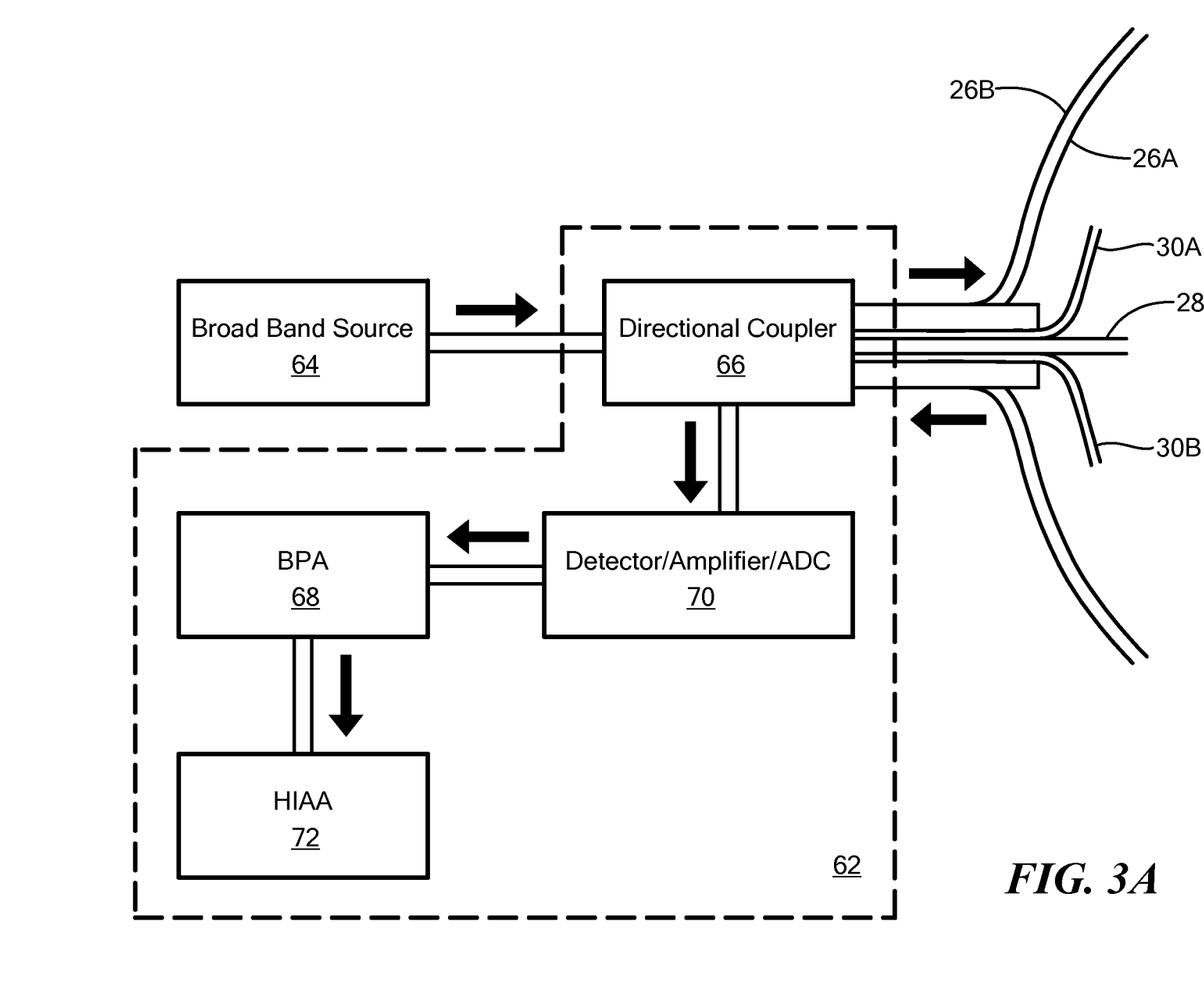
FIG. 3A shows a schematic view of a first exemplary processing unit and light source.
Figure 3B:
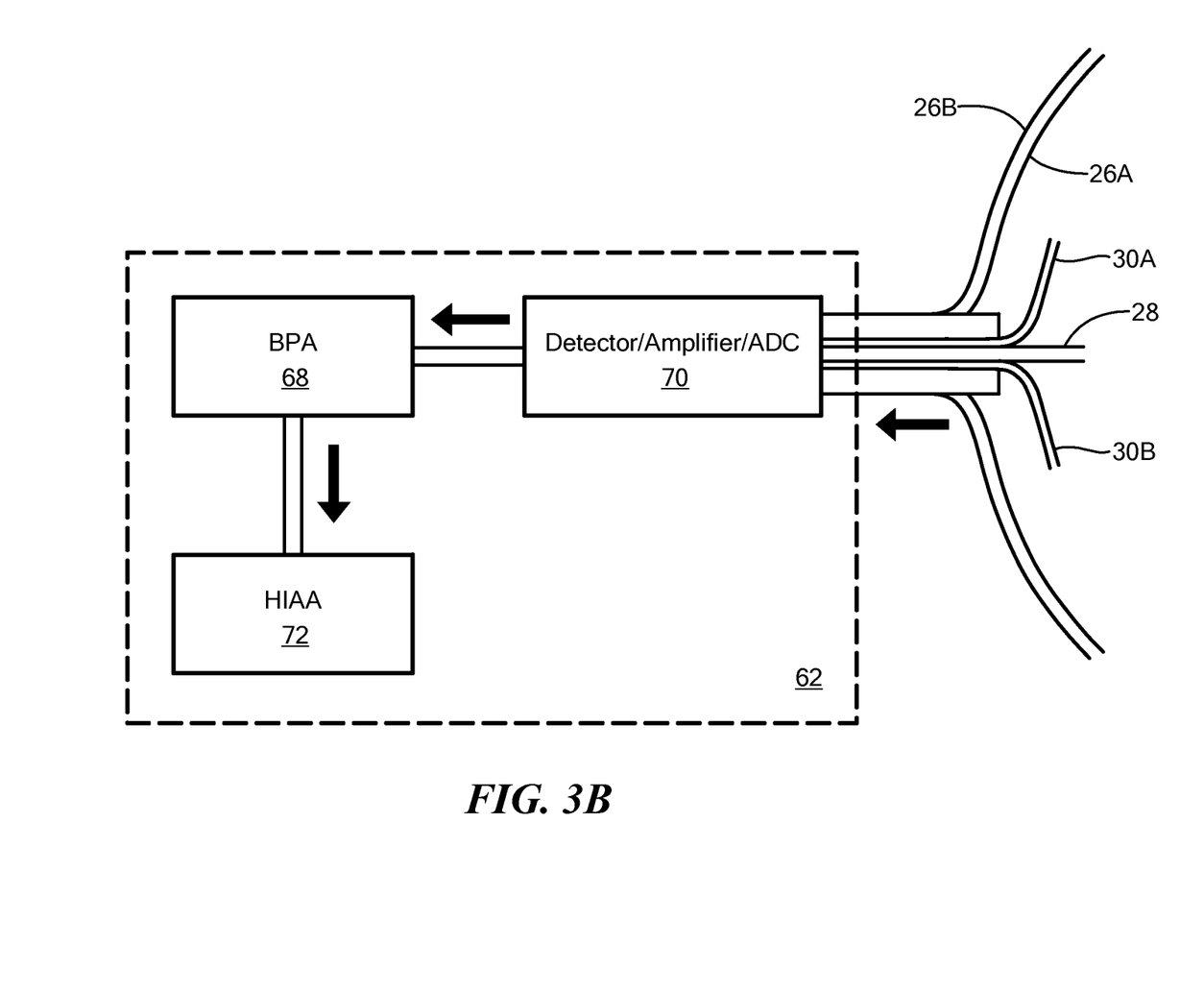
FIG. 3B shows a schematic view of a second exemplary processing unit without a light source.

Specifically, as is shown in FIG. 3A, the console 14 may optionally include a light source 64 (such as a broadband light source or laser optical source) that directs light through the one or more fiber sensors 30 and a directional coupler 66, although light may be transmitted from the one or more fiber sensors 30 to the processing unit 62 without the use of a light source 64, as shown in FIG. 3B. For example, the one or more fiber sensors 30 may receive and transmit light that is naturally emitted from the tissue without the use of a light source. That is, the light received and transmitted by the one or more fiber sensors may be emitted from (or produced by) the tissue rather than light that is delivered from a light source and reflected, refracted, and/or scattered by the tissue. As is described in more detail below, light that is emitted and/or reflected from tissue may travel back through the one or more fiber sensors 30, through the directional coupler 66, through a detector/amplifier/analog-to-digital converter (ADC) 70, and into a beam processing apparatus (BPA) 68. Data from the BPA 68 may then be transmitted to a hyperspectral imaging and analysis apparatus (HIAA) 72 for hyperspectral imaging and data analysis.

However, use of the light source 64 is optional because the fiber sensor 30 of the device may be configured to be in direct contact with the tissue through the first 26A and second 26B cryoballoons. The cryoballoons 26A, 26B may be optically tuned to collect any light naturally emitted, radiated, and/or reflected from the tissue. For example, this optical tuning may be achieved by selecting the appropriate refractive indices, thicknesses, grating modulations, or the like. Ablated tissue (immediately after ablation and before temperature homogenization) may exhibit a high thermal contrast against surrounding tissue that provides enough radiation to allow for the physical discernment between ablated and non-ablated tissue. The thermal contrast may be discernible despite the scattering and absorption by blood. Via evanescent coupling, electromagnetic waves are transmitted from the tissue to the fiber sensor 30 (through the one or more cryoballoons 26) by means of the evanescent, exponentially decaying electromagnetic field. The cryoballoon 26 (or outer cryoballoon if more than one cryoballoon is used) is positioned in direct contact with tissue, thus placing the fiber sensor 30 in very close proximity to the tissue. Having the cryoballoon 26 inflated during sensing may minimize the effect of blood flow due to heart motion during image or spectrum acquisition. The HIAA 72 may minimize heart motion further by executing one or more algorithms for motion compensation. The fiber sensor 30 is configured to support modes (or light wave propagation pattern) of the appropriate frequency that is emitted from the tissue, and the emitted light is thereby connected or coupled to the fiber sensor 30. The light emitted, radiated, and/or reflected from the tissue may be collected and conveyed to the BPA 68. This light may be dispersed into different wavelengths by a dispersing element (for example, grating, C-band wavelength-division multiplexing, or the like). This dispersed light may then be collected by a detector, such as a bolometer or CCD, as a two-dimensional image (X, λ) where X represents the spatial dimension or swath and λ represents the spectral dimension. The fiber sensor 30, may be rotated within the balloon 26 against the tissue to enable collection of different swaths and development of the hypercube (X, Y, λ), where Y represents the second spatial dimension.

Figure 8:
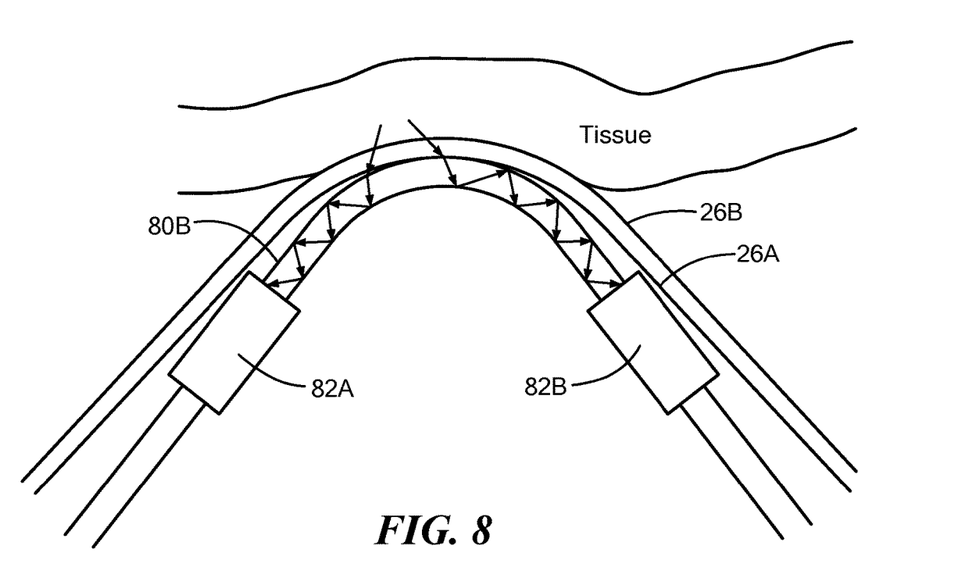
FIG. 8 shows a cross-sectional view of a portion of the cryotreatment device of FIG. 7.
Figure 10:
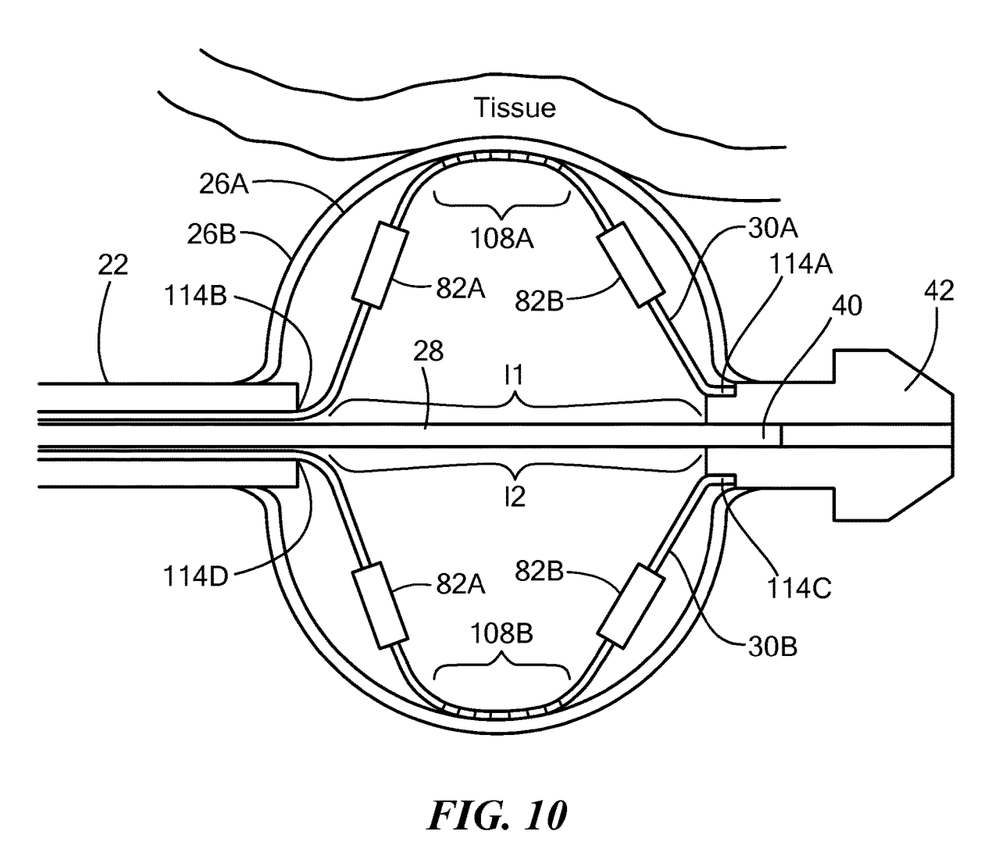
FIG. 10 shows simplified depictions of a cryotreatment device having fiber sensors including an optical grating within the core.

As discussed above, the cryotreatment catheter 12 may include a cryoballoon 26 having a proximal neck 36 coupled to the distal portion 22 of the elongate body 20 and a distal neck 38 coupled to the distal portion 40 of the shaft 28. The distal portion 40 of the shaft 28 may also be coupled to or integrated with a distal tip 42, and the distal neck 38 may be coupled to the distal portion of the shaft 28 and/or the distal tip 42. However, it will be understood that the cryoballoon 26 may be coupled to the elongate body 20 and/or shaft 28 in other suitable configurations. Further, FIGS. 7, 8, and 10 show an embodiment in which the treatment element includes an inner cryoballoon 26A and an outer cryoballoon 26B. Such a configuration may enhance patient safety, as the outer balloon may prevent refrigerant from entering the patient's bloodstream if the inner balloon developed a leak. The cryoballoon 26, or the inner cryoballoon 26A in the two-balloon configuration, may also define an inner chamber 74 in which refrigerant is expelled from the fluid injection lumen 46 through one or more injection elements 76. For example, the injection element 76 may include a conduit that is wrapped around the shaft 28 in one or more coils, and may have a plurality of injection apertures (not shown). Refrigerant expelled into the inner chamber 74 may be drawn from the chamber 74 and into the fluid recovery lumen 50 by the negative pressure environment generated by the vacuum 54, with which the fluid recovery lumen 50 may be in fluid communication. Recovered refrigerant may be vented to the atmosphere or collected in the refrigerant recovery reservoir 52. Although the treatment element 26 is shown and described herein as being a cryoballoon 26, it will be understood that the treatment element 26 may be any structure capable of ablating tissue and retaining refrigerant within.

The one or more fiber sensors 30 may transmit light from ablated tissue, such as radiated, emitted, scattered, and/or reflected light, to the console 14 for processing and analysis by the processing unit 62. As a non-limiting example, the one or more fibers 30 may be composed of materials known in the art to be suitable for fiber optics applications, including but not limited to sol-gel material. Polyglass-based sol-gel materials demonstrate acceptable optical loss for broadband wavelengths (0.6 m to 10.8 µm). Polyglass is an organic/inorganic glass material made by the sol-gel method (polycondensation and pohtopolymerization of metallic alkoxides), and the metallic components and the UV dose may be employed for refractive index tuning.

Figure 4A:
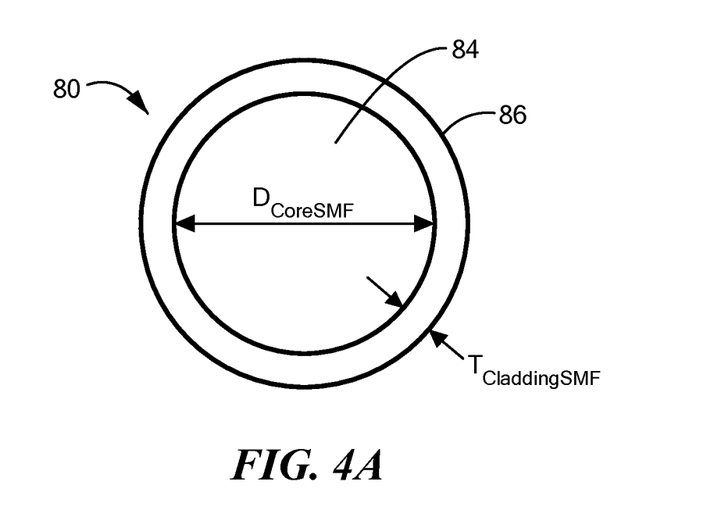
FIG. 4A shows a cross-sectional view of a singlemode fiber.
Figure 4B:
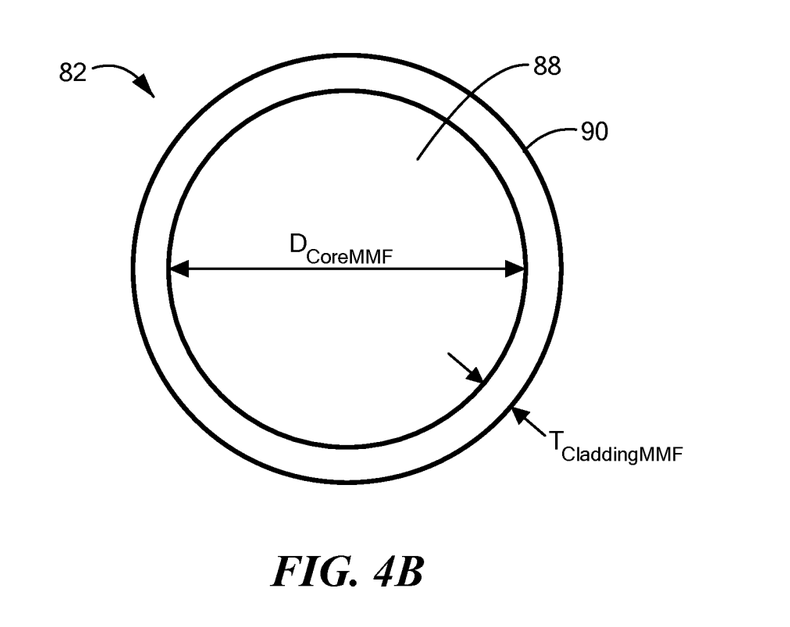
FIG. 4B shows a cross-sectional view of a multimode fiber.

As discussed above, the fiber sensor 30 of the device may be configured to collect the electromagnetic waves from the ablated tissue and non-ablated tissue through evanescent coupling. Each fiber sensor 30 may be a singlemode-multimode-singlemode (SMS) fiber structure that includes at least one step index singlemode fiber (SMF) 80 and at least one step index multimode fiber (MMF) 82. As shown in FIG. 4A, the SMF 80 may have a core 84 having a diameter $D_{CoreSMF}$, a cladding 86 having a thickness $T_{CladdingSMF}$, a length, and a difference refractive index (cladding refractive index/core refractive index) optimized for maximum evanescent field coupling coefficient. Likewise, as shown in FIG. 4B, the MMF 82 may have a core 88 having a diameter $D_{CoreMMF}$, a cladding 90 having a thickness $T_{CladdingMMF}$, a length, and a difference refractive index optimized for maximum coupling of modes from SMF to core and cladding modes of the MMF. The diameter $D_{CoreMMF}$ of the MMF core 88 may be larger than the diameter $D_{CoreSMF}$ of the SMF core 84. The MMF 82 may be fusion spliced to the SMF 80 so as to minimize optical loss.

Figure 5A:
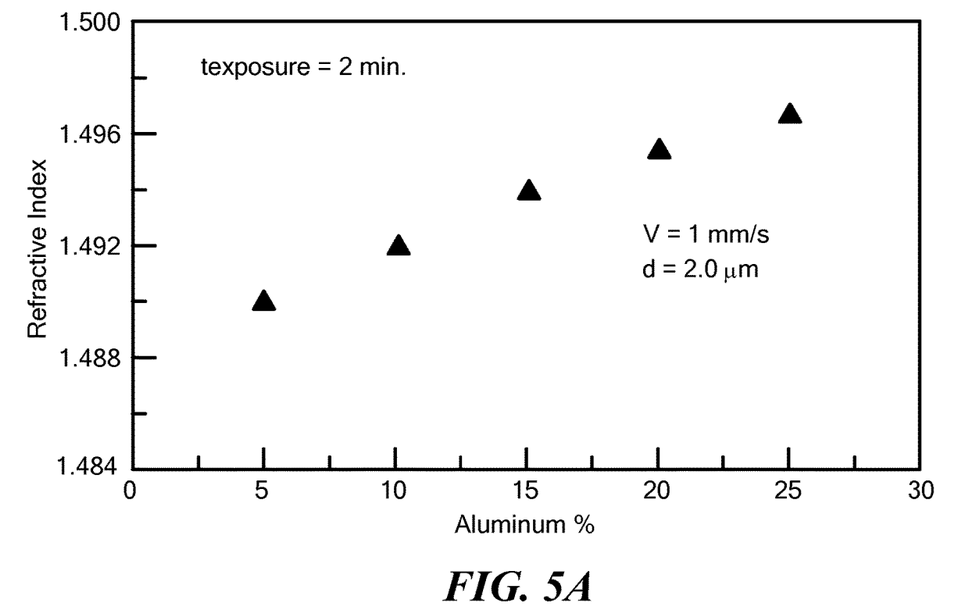
FIGS. 5A and 5B show dependence of the refractive index of a material on the percent composition of aluminum (Al) and zirconium (Zr), respectively.
Figure 5B:
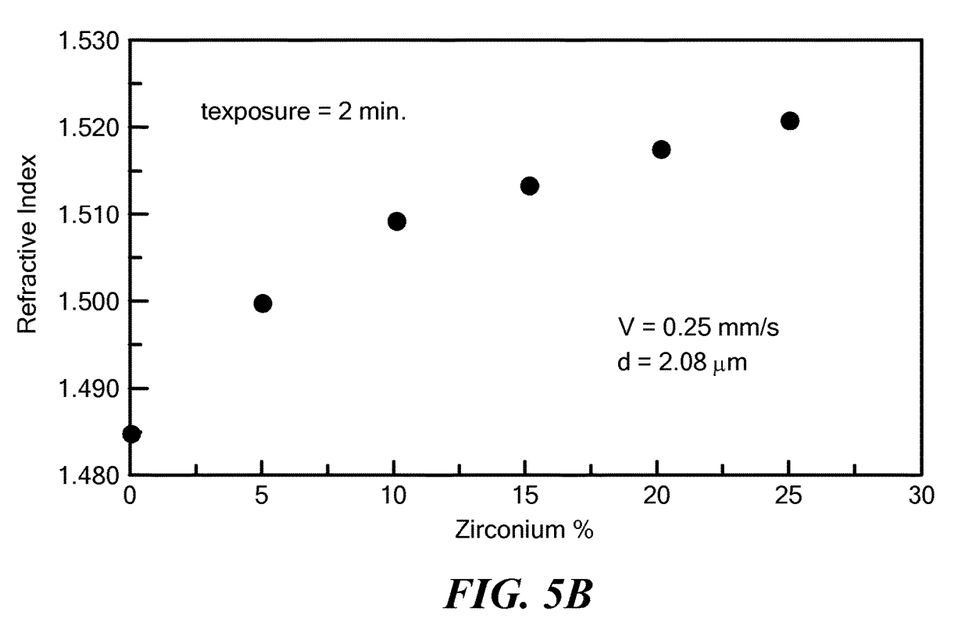

Hybrid $(1-x)SiO_2\text{-}xZrO_2$, $(1-x-y)SiO_2\text{-}xAl_2O_3\text{-}yP_2O_5$, and $(1-y)SiO_2\text{-}7yAl_2O_3$ sol-gel solutions may be prepared using Methaciyloxypropyltrioxysilane (MAPTMS) hydrolyzed with 1.5 equivalents of $H_2O$, and with 0.1 M HCl as a catalyst. Further, $Zr(OC_3H_7)_4$, which may be used as a refractive index modifier, may be dissolved in isopropanol in a 1:1 volume ratio and then the mixture may be added dropwise to the stirred solution of the partially hydrolyzed MAPTMS. After adding water to complete the hydrolyzation of alkoxide substituents, Irgacure 184 (Ciba Specialty Chemicals Inc., Basel, Switzerland) may be introduced as a photoinitiator. The adjustment of chemical composition of the raw materials, ultraviolet light exposure, and heat treatment provides precise selection of refractive index from 1.48 to 1.52 at a wavelength of 632.8 nm. This organically modified glass fabric belongs to the class of hybrid organic-inorganic glasses known variously as "ormocers" (organically modified ceramics), "ormosils" (organically modified silicates), "ceramers," "polycerams," or simply hybrid sol-gel glasses (HSGG). Optical devices may be rapidly prototyped with HSGG because (1) homogenous thick films can be precision deposited without cracks in a single step; (2) a large menu of organically modified materials may be synthesized to quickly adapt to specific device requirements;

and (3) HSGGs offer a singular advantage in being able to resolve conflicting material demands of the device. The essence of this flexibility may be found in the coupling of the attractive features of organic polymers with those of inorganic glasses. FIGS. 5A and 5B depict the dependence of the refractive index of the films on the percentage composition of aluminum (Al) and zirconium (Zr), respectively. The fiber sensor 30 may be made using one or more variants of the HSGG material to have the refractive indices tuned to optimize light coupling from the tissue.

Figure 6:
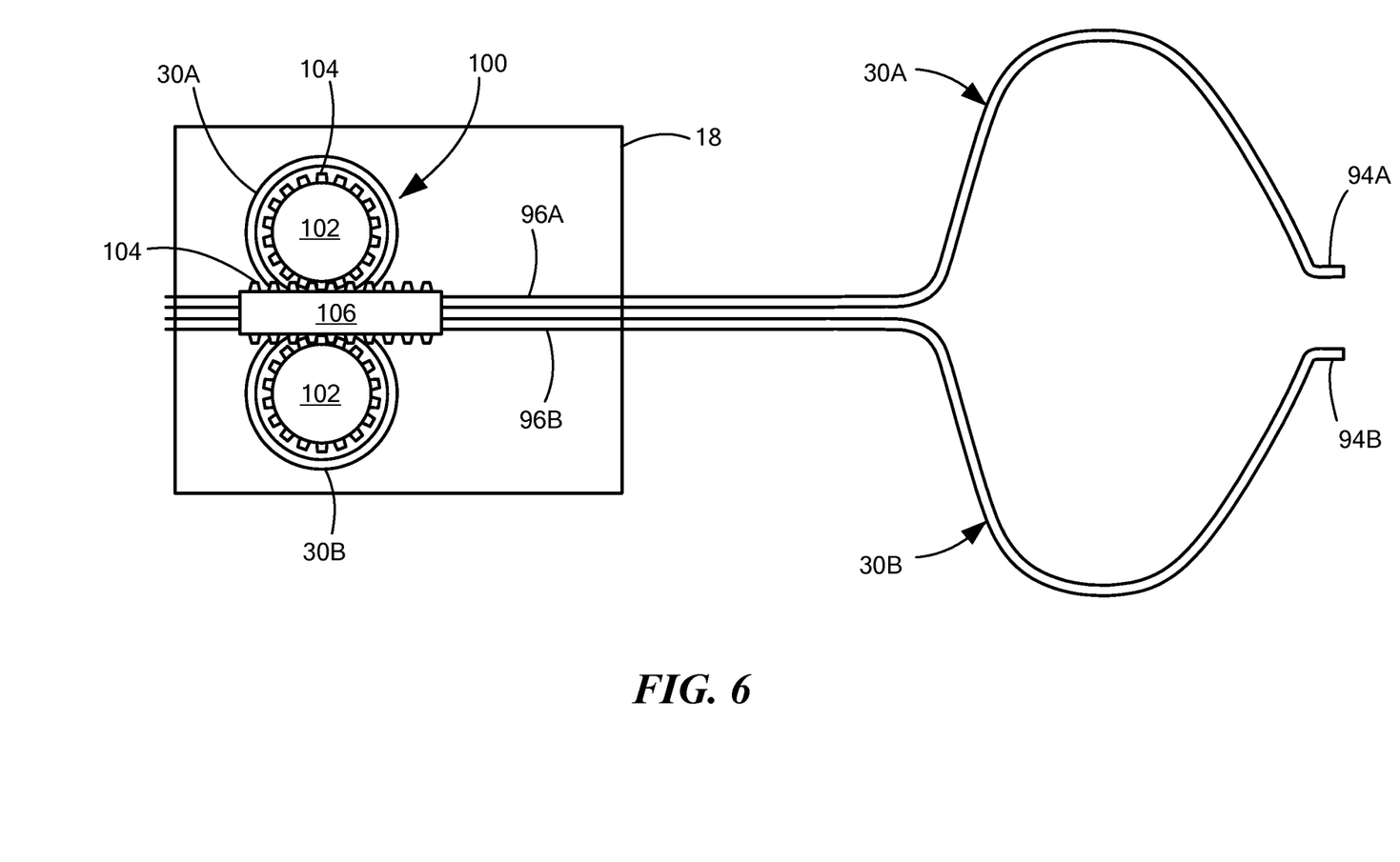
FIG. 6 shows a first fiber sensor and a second fiber sensor coupled to a rotary mechanism, the rotary mechanism located within a device handle.

The cryotreatment catheter 12 may have a first fiber sensor 30A and a second fiber sensor 30B that are diametrically positioned within the inner chamber 74. The distal portion 94A, 94B of each fiber sensor 30A, 30B, respectively, may be attached to a portion of the shaft 28, for example, at a location at or proximate the distal portion 40, and optionally may be attached to a rotating mechanism 95 coupled to the distal tip 42. In contrast, the proximal portion 96A, 96B of each fiber sensor 30A, 30B, respectively, may not be coupled to the shaft 28 and instead may freely move longitudinally within the inner chamber 74 and the elongate body 20. For example, the proximal portions 96A, 96B may be coupled to or otherwise engaged with a rotary mechanism 100 located within the handle 18 (shown in FIG. 6). The rotary mechanism 100 may allow longitudinal movement of the fiber sensors 30A, 30B within the inner chamber 74 and the elongate body 20 as the balloon is inflated and deflated while maintaining a tension in the fiber sensors 30A, 30B so they do not buckle, bunch, or interfere with the cryotreatment procedure. The rotating mechanism 95 may be rotated clockwise or counterclockwise around the longitudinal axis 34 of the device. As a non-limiting example, the rotary mechanism 100 may include a spool 102 for each fiber sensor 30A, 30B. Each fiber sensor 30A, 30B may be wound about a spool 102, and the spools 102 may include teeth or protrusions 104 that may be interdigitated with teeth or protrusions 104 on a base unit 106. As the spools 102 are rotated, the fiber sensors 30A, 30B may be wound or unwound about the spools 102.

Blood includes several components, including plasma (typically about 55% total volume), white blood cells and platelets (typically less than 1% total volume), and red blood cells (typically about 45% total volume). The typical composition of plasma is about 92% water, about 7% proteins, and about 1% mineral salt, sugars, fats, and hormones. Imaging or sensing through blood is driven by the optical characteristics of blood: (1) absorption of radiation by hemoglobin and water; and (2) scattering of radiation by red blood cells. There are wavelength ranges (1.4-1.8 microns, 2.1-2.4 microns, 3.7-4.3 microns, 4.6-5.4 microns, and 7-12 microns) at which the desirable characteristics of low scattering of light by suspended red blood cells and low absorption of radiation by hemoglobin and water occur. Thus, the light source 64 may be used to transmit light to the one or more fiber sensors 30 at a wavelength within one or more of these ranges. Alternatively, the system may include only a processing unit 62 configured to sense reflected/emitted light from tissue without the light source 64 (for example, as shown in FIG. 3B). It has been shown that ablated tissue (that is, immediately after ablation and before temperature homogenization) exhibits high thermal contrast compared to surrounding unablated tissue and provides enough radiation to be sensed by off-the-shelf high-sensitivity bolometers without the aid of an external light source.

Therefore, certain wavelengths of light may be advantageously used for hyperspectral data acquisition. A broadband source having the advantageous wavelengths may be used to illuminate the tissue to reveal spectral features and discern between ablated and non-ablated tissue. Within certain wavelength ranges (for example, 1.4 to 1.8 microns), radiation scattering by red blood cells in plasma and absorption by water and hemoglobin may be drastically reduced. Thus, if a light source 64 is used, the light source 64 may be selected to have a wavelength in the range of 1.4 to 1.8 microns so the collected light can also be between 1.4 and 1.8 microns.

Alternatively, the light source 64 may be selected to have a wavelength in the range of 7 to 12 microns so the collected light can also be between 7 to 12 microns. Within this range, the radiation may be the least likely to be scattered by red blood cells, absorption of radiation by water and hemoglobin may be reduced, and tissue may radiate energy having a wavelength within the range of 2 to 12 microns, depending on the tissue's inherent temperature. Still further, it will be understood that the light source 64 may be configured to deliver light having any of a variety of wavelengths, so that the desired wavelength may be selected for a particular procedure.

Although ultraviolet (UV) light is the most scattered light by the blood and has the smallest tissue penetration depth, the fiber sensor 30 in direct contact with the tissue may passively gather any emitted, radiated, or reflected wavelength in the range of 0.35 to 0.5 microns. Using a light source to have a wavelength in the range of 0.35 to 0.5 microns may excite the collagen within the tissue, which may in turn fluoresce to illuminate the muscle layers beneath. The reflected light from the ablated muscle may be collected by the fiber sensor 30 and then analyzed by the HIAA.

Figure 9:
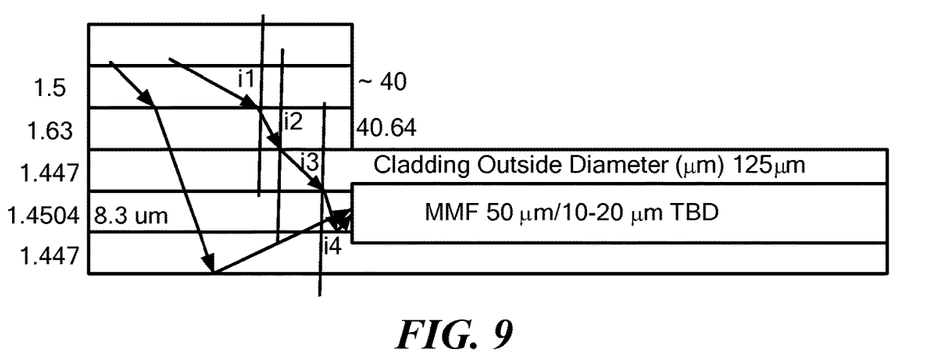
FIG. 9 shows movement of light from tissue through a series of materials and into a core of multimode fiber segment.

FIG. 7 shows an exemplary placement of a two-cryoballoon treatment element in direct contact with target tissue for receiving emitted and/or reflected light from the tissue through evanescent coupling. Having the balloons 26A, 26B inflated during sensing may minimize the effect of blood flow around the measured tissue. When the treatment element is in contact with the tissue, the tissue, the outer cryoballoon 26B, the inner cryoballoon 26A, and the fiber sensor 30 may form a stack of layers of varying refractive indices, as shown in FIG. 9. As a non-limiting example for illustration, the outer cryoballoon 26B may be composed of polyurethane with a refractive index of 1.5 measured at wavelength 632.8 nm and the inner cryoballoon 26A may be composed of polyethylene terephthalate having a refractive index of 1.63 measured at wavelength 632.8 nm. The SMF cladding 86 may have a refractive index of, for example, 1.447 and the SMF cladding 88 may have a refractive index of approximately 1.4504. Non-limiting thicknesses of the cladding, cores, and cryoballoons are shown in FIG. 9 for illustration only. The outer cryoballoon 26B and/or inner cryoballoon 26A may be selected to have a refractive index for optimal refraction of one or more spectra of interest and may be different than the exemplary characteristics shown in FIG. 7.

As shown in FIGS. 8 and 9, the light emitted or radiated from the tissue may be first refracted in total or in part through the outer cryoballoon 26B to the inner cryoballoon 26A, and then to, for example, the cladding 86 of the SMF 80. The cladding modes in the SMF 80 may enter the core of the MMF 82. For example, the cryotreatment catheter 12 may include a first MMF segment 82A at a location proximal to the SMF 80B segment being in contact with the target tissue (through cryoballoons 26A, 26B) and a second MMF segment 82B at a location distal to the SMF 80C segment being directed toward the target tissue. Put another way, the first MMF segment 82A may be located between a first 80A and a second 80B SMF segment and the second MMF segment 82B may be located between the second 80B and a third 80C SMF segment (as shown in FIG. 7).

The light may then travel through the fiber sensor 30 to the console 14. Specifically, the light (electromagnetic radiation) may pass through the directional coupler 66 and into the BPA 68. The BPA 68 may include a grating, broadband infrared detector (such as a combination of a bolometer and III-V semiconductor detector), and readout electronics such as a converter circuit, signal sampling and signal integrity multiplexer. For example, a bolometer in the BPA 68 may measure the power of the incident electromagnetic radiation (light). The BPA 68 may convert the optical signal to an electrical signal including a plurality of pixels 33 and perform signal processing (for example, non-uniformity correction, coarse pixel correction, and cross-talk reduction). Further, the BPA 68 may correlate each pixel 33 to a spectrum of light. The term "spectrum" may refer to amplitude and/or intensity of radiation across a range of wavelengths. The signal of each pixel 33 in the form of a spectrum is then transmitted to the HIAA 72 for hyperspectral data analysis. The HIAA 72 may process wavelengths of radiation in the long-infrared range of the electromagnetic spectrum to determine "hot spots," or areas of tissue having a higher heat signature. Tissue ablated using cryoablation will register a lower heat signature than areas of non-ablated tissue. Further, the HIAA 72 may compare the acquired spectral data to reference spectral data. For example, the HIAA 72 may compare the spectrum of each pixel 33 to a reference spectrum of an ablated tissue. The processing unit 62 may communicate this data to the user, such as by displaying a heat signature map, hyperspectral image of the tissue, and/or spectral data. The HIAA 72 may further be programmed or programmable to execute one or more algorithms that allow for compensation for motion caused by the beating heart.

Light emitted from the light source 64 optionally may be conveyed by the first SMF segment 80A into the core 88 and cladding 90 of MMF 82, and then may be conveyed to the second SMF segment 80B as a result of interference. The second SMF segment 80B may be polished and treated for maximum reflection. As per reciprocity, the reflected light may then be subject to the same optical path. Light reflected from the second SMF segment 80B may then excite the core 88 and cladding 90 of the MMF 82 and then be conveyed into the first SMF segment 80A. The transmitted light may be wavelength dependent, that is, may depend on the blood optical characteristics. Further, an isolator may be used to prevent reflected light from interfering with the light source 64. The directional coupler 66 may guide the reflected light toward the BPA 68 to process the conveyed light.

Figure 11:
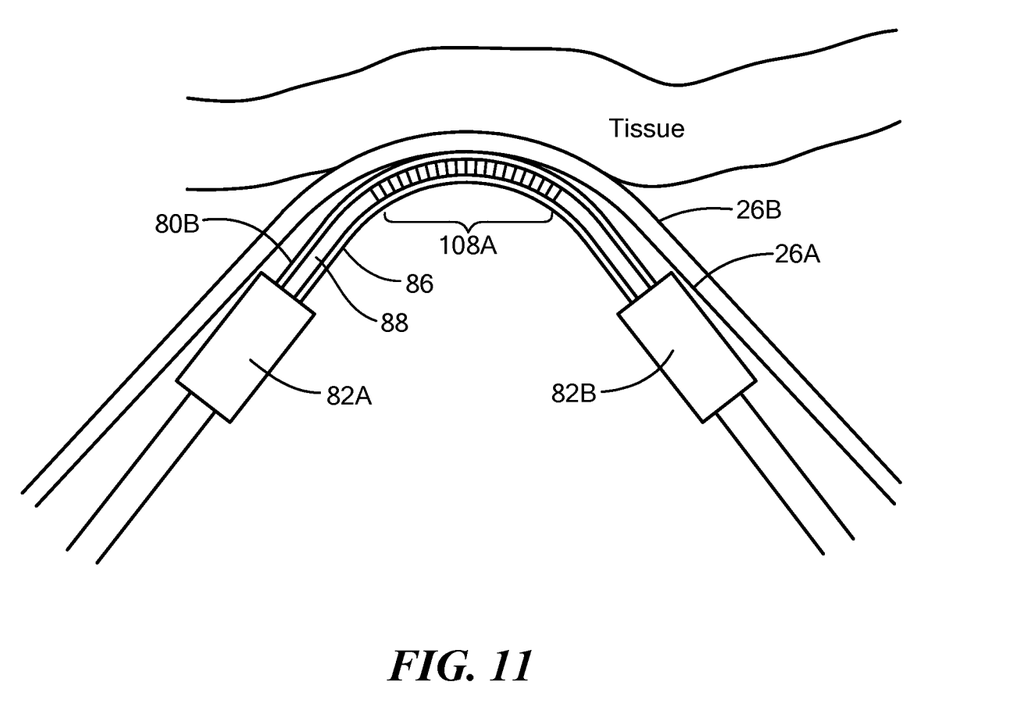
FIG. 11 shows a close-up, cross-sectional view of the cryotreatment device of FIG. 10.

Referring now to FIG. 10, a cross-sectional view of the device is shown, with a simplified depiction of the fiber sensors. The fiber sensors 30A, 30B may include one or more SMF waveguide segments 80 and one or more MMF waveguide segments 82, as discussed above. Regardless of the configuration of the fiber sensors 30A, 30B, the core 88 may include grating such as a long-period grating (LPG) 108A, 108B. The fiber sensors 30A, 30B are shown in FIG. 10 as though the grating 108 is on the outer surface of the fiber sensors 30A, 30B, but this is for simplicity of the figures. FIG. 11 shows a close-up view of the fiber sensor 30A having grating 108A within its core 88. The grating 108 may be created by a local refractive index modulation as a result of a photo-inscription by an ultraviolet (UV) illumination source. Light transmitted through the core 88 of each fiber sensor may be affected by the grating 108.

The grating 108 may be configured to be in contact with the inner surface of the first cryoballoon 26A. Coupling light through the grating 108 is possible when the periodicity of the grating is selected to satisfy a phase-matching condition between the two coupled optical modes. The coupling is effective when the grating period is selected such that the grating-assisted scattering of light from the first cryoballoon 26A to the cladding 86 mode is in resonance with the core 88 mode. This takes place when the period of the grating $\Lambda$ (nm) satisfies the following phase-matching conditions:

$$\Lambda \text{ (nm)} = \lambda/(n_{\mathit{eff}}\text{Core} - n_{\mathit{eff}}\text{CL}) \quad (1)$$

in which $n_{\mathit{eff}}$Core and $n_{\mathit{eff}}$CL are the effective refractive indices of the core 88 and cladding 86 modes of fiber 30, respectively, and $\lambda$ is the resonant wavelength.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device comprising:
    an elongate body including a distal portion, a proximal portion, and a first longitudinal axis;
    an inflatable treatment element having an inner chamber and defining a second longitudinal axis, at least a portion of the inflatable treatment element being coupled to the distal portion of the elongate body;
    a shaft; and
    a fiber sensor having:
        a distal portion;
        a proximal portion, the proximal portion being freely movable along the second longitudinal axis of the inflatable treatment element and along the first longitudinal axis of the elongate body;
        a first singlemode waveguide segment;
        a second singlemode waveguide segment;
        a third singlemode waveguide segment;
        a first multimode waveguide segment; and
        a second multimode waveguide segment, the first multimode waveguide segment located between the first singlemode waveguide segment and the second singlemode waveguide segment, and the second multimode waveguide segment located between the second singlemode waveguide segment and the third singlemode waveguide segment, at least one of the first, second, and third singlemode waveguide segments configured to have a first difference refractive index and at least one of the first and second multimode waveguide segments configured to have a second difference refractive index, the first difference refractive index being different from the second difference refractive index, at least a portion of the fiber sensor being located within the inflatable treatment element, the fiber sensor being slidably disposed within the shaft.

2. The device of claim 1, wherein the inflatable treatment element defines an interior surface, the fiber sensor being configured to be in contact with at least a portion of the interior surface when the inflatable treatment element is inflated.

3. The device of claim 1, wherein the shaft has a proximal portion and a distal portion, the shaft being longitudinally movable within the elongate body and at least a portion of the distal portion of the shaft being located within the inflatable treatment element.

4. The device of claim 3, wherein the inflatable treatment element includes a proximal neck and a distal neck, the distal neck being coupled to the distal portion of the shaft and the proximal neck being coupled to the distal portion of the elongate body.

5. The device of claim 4, further including a handle coupled to the proximal portion of the elongate body, the handle including a rotary mechanism, the proximal portion of the fiber sensor being engaged with the rotary mechanism.

6. The device of claim 1, wherein the inflatable treatment element further includes an outer surface and the outer surface of the inflatable treatment element is configured to be in contact with an area of target tissue when the inflatable treatment element is inflated.

7. A medical device for determining whether an area of tissue has been ablated, the device comprising:
an elongate body having a distal portion, a proximal portion, and a first longitudinal axis;
an inflatable treatment element at the distal portion of the elongate body having an inner chamber and defining a second longitudinal axis;
a shaft defining a lumen and having a distal portion and a proximal portion, at least a portion of the shaft being located within the inflatable treatment element; and
a first fiber sensor and a second fiber sensor each having:
a distal portion;
a proximal portion opposite the distal portion, the proximal portion of the first fiber sensor and the second fiber sensor each being freely movable along the second longitudinal axis of the inflatable treatment element and along the first longitudinal axis of the elongate body;
a first singlemode waveguide segment;
a second singlemode waveguide segment;
a third singlemode waveguide segment;
a first multimode waveguide segment; and
a second multimode waveguide segment, the first multimode waveguide segment located between the first singlemode waveguide segment and the second singlemode waveguide segment, and the second multimode waveguide segment located between the second singlemode waveguide segment and the third singlemode waveguide segment, at least one of the first, second, and third singlemode waveguide segments configured to have a first difference refractive index and at least one of the first and second multimode waveguide segments configured to have a second difference refractive index, the first difference refractive index being different from the second difference refractive index, and each configured to transmit optical data from the area of tissue, at least a portion of each of the first and the second fiber sensors being located within the inflatable treatment element and having a core and a cladding, the core of each of the first and the second fiber sensors having an optical grating.

8. The device of claim 7, wherein each of the first and the second fiber sensors is longitudinally movable within the shaft.

9. The device of claim 7, wherein the inflatable treatment element defines an inner surface and an outer surface, and the cladding of each of the first and the second fiber sensors is configured to be in contact with the inner surface when the inflatable treatment element is inflated.

10. The device of claim 9, wherein light from the tissue is coupled from the inflatable treatment element to the cladding of at least one of the first and the second fiber sensors at an area of contact between the at least one of the first and the second fiber sensors and the inflatable treatment element.

11. The device of claim 10, wherein the optical grating includes a period $\Lambda$ (nm), the period $\Lambda$ being selected according to an equation:

$$\Lambda \text{ (nm)} = \lambda/(n_{\textit{eff}}\text{Core} - n_{\textit{eff}}\text{CL}),$$

wherein $n_{\textit{eff}}$Core is an effective refractive index of the core, $n_{\textit{eff}}$CL is an effective refractive index of the cladding, and $\lambda$ is the resonant wavelength of the light from the tissue.

12. A medical system for determining whether an area of tissue has been ablated, the system comprising:
a device including:
an elongate body having a distal portion, a proximal portion, and a first longitudinal axis;
an inflatable treatment element at the distal portion of the elongate body having an inner chamber and defining a second longitudinal axis;
a shaft defining a lumen and having a distal portion and a proximal portion, at least a portion of the shaft being located within the inflatable treatment element; and
at least one fiber sensor having:
a distal portion;
a proximal portion opposite the distal portion, the proximal portion of the at least one fiber sensor being freely movable along the second longitudinal axis of the inflatable treatment element and along the first longitudinal axis of the elongate body;
a first singlemode waveguide segment;
a second singlemode waveguide segment;
a third singlemode waveguide segment;
a first multimode waveguide segment; and
a second multimode waveguide segment, the first multimode waveguide segment located between the first singlemode waveguide segment and the second singlemode waveguide segment, and the second multimode waveguide segment located between the second singlemode waveguide segment and the third singlemode waveguide segment, at least one of the first, second, and third singlemode waveguide segments configured to have a first difference refractive index and at least one of the first and second multimode waveguide segments configured to have a second difference refractive index, the first difference refractive index being different from the second difference refractive index, the at least one fiber sensor configured to transmit optical data from the area of tissue, at least a portion of the at least one fiber sensor being located within the inflatable treatment element and having a core and a cladding, the core of the at least one fiber sensor having a long-period grating; and
a processing unit in communication with the at least one fiber sensor, the processing unit including:
a beam processing apparatus configured to receive optical data transmitted through the fiber sensor; and a hyperspectral imaging and analysis apparatus in communication with the beam processing apparatus and configured to generate a hyperspectral image based on the optical data received by the beam processing apparatus.

13. The system of claim 12, wherein the beam processing apparatus includes a grating and a broadband infrared detector.

14. The system of claim 12, wherein the beam processing apparatus is configured to convert an optical signal received from the fiber sensor to an electrical signal including a plurality of pixels.

15. The system of claim 14, wherein the beam processing apparatus is further configured to correlate each pixel to a spectrum value.

16. The system of claim 15, wherein the hyperspectral imaging and analysis apparatus is configured to compare the spectrum value of each pixel to a reference spectrum value of ablated tissue.

17. The system of claim 16, wherein the hyperspectral imaging and analysis apparatus further is configured to determine whether the area of tissue is ablated based at least in part on the comparison.

\* \* \* \* \*